United States Patent
Baney et al.

(10) Patent No.: US 8,939,959 B2
(45) Date of Patent: Jan. 27, 2015

(54) DOSE DIVIDING DELIVERY DEVICE

(71) Applicant: Becton, Dickinson and Company, Franklin Lakes, NJ (US)

(72) Inventors: Bruno Baney, Claix (FR); Colin May, London (GB); Patrick Dupuis, Jarrie (FR); Frederic Perot, Saint Paul de Varces (FR)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 13/922,779

(22) Filed: Jun. 20, 2013

(65) Prior Publication Data

US 2013/0289493 A1 Oct. 31, 2013

Related U.S. Application Data

(63) Continuation of application No. 12/864,685, filed as application No. PCT/IB2008/001028 on Jan. 30, 2008, now abandoned.

(51) Int. Cl.
| | | |
|---|---|---|
| *A61M 31/00* | (2006.01) | |
| *A61M 5/00* | (2006.01) | |
| *A61M 5/315* | (2006.01) | |
| *A61M 5/31* | (2006.01) | |
| *A61M 5/32* | (2006.01) | |

(52) U.S. Cl.
CPC ....... *A61M 5/31526* (2013.01); *A61M 5/31595* (2013.01); *A61M 5/3134* (2013.01); *A61M 5/3243* (2013.01); *A61M 5/3293* (2013.01)
USPC ........... 604/506; 604/500; 604/181; 604/187; 604/207; 604/208; 604/210; 604/218

(58) Field of Classification Search
USPC ......... 604/506, 181, 187, 207, 208, 209, 210, 604/211, 218, 500, 220, 224
See application file for complete search history.

(56) References Cited

U.S. PATENT DOCUMENTS

| | | | |
|---|---|---|---|
| 315,292 A | 4/1885 | Howell | |
| 1,393,720 A | 10/1921 | Lomas et al. | |
| 2,373,520 A | 4/1945 | Wallin | |
| 2,409,656 A | 4/1945 | Austin | |
| 2,502,639 A | 4/1950 | Blake | |
| 2,695,023 A * | 11/1954 | Brown | 604/210 |
| 2,707,954 A | 5/1955 | Kas | |
| 2,764,981 A | 10/1956 | Helmer et al. | |
| 2,875,761 A | 3/1959 | Helmer et al. | |

(Continued)

FOREIGN PATENT DOCUMENTS

| | | |
|---|---|---|
| CH | 293 302 | 9/1953 |
| DE | 10 06 589 | 4/1957 |

(Continued)

*Primary Examiner* — Kevin C Sirmons
*Assistant Examiner* — Shefali Patel
(74) *Attorney, Agent, or Firm* — Robert E. West

(57) ABSTRACT

A simple method and device enabling a unit dose from a reservoir is provided. The dose is drawn into the reservoir and is then expelled from the device by depressing a plunger. The plunger has features which divide the dose into discrete intervals. As the plunger is moved during delivery, the features on the plunger and features connected to a barrel interact to provide for intermittent stops to the delivery. Other aspects of the device provide for reduced dead space, safety and selective interconnection with other devices. Thus, the device divides the dose.

32 Claims, 13 Drawing Sheets

(56) References Cited

U.S. PATENT DOCUMENTS

| | | | |
|---|---|---|---|
| 2,895,473 A | 7/1959 | Reznek | |
| 3,281,023 A | 10/1966 | Bruck et al. | |
| 3,747,812 A | 7/1973 | Karman et al. | |
| 3,863,632 A * | 2/1975 | Schwartz | 604/170.01 |
| 3,949,748 A | 4/1976 | Malmin | |
| 4,022,207 A | 5/1977 | Citrin | |
| 4,050,459 A | 9/1977 | Sanchez | |
| 4,099,548 A | 7/1978 | Sturm et al. | |
| 4,246,898 A | 1/1981 | Travalent et al. | |
| 4,312,343 A | 1/1982 | LeVeen et al. | |
| 4,466,426 A | 8/1984 | Blackman | |
| 4,475,905 A | 10/1984 | Himmelstrup | |
| 4,592,745 A | 6/1986 | Rex et al. | |
| 4,592,746 A | 6/1986 | Burkholder et al. | |
| 4,610,672 A | 9/1986 | Ewalt et al. | |
| 4,642,102 A | 2/1987 | Ohmori | |
| 4,659,327 A | 4/1987 | Bennett et al. | |
| 4,810,249 A | 3/1989 | Haber et al. | |
| 4,950,163 A | 8/1990 | Zimble | |
| 5,024,661 A | 6/1991 | Wender et al. | |
| 5,032,114 A | 7/1991 | Olovson | |
| RE33,821 E | 2/1992 | Banks | |
| 5,226,895 A | 7/1993 | Harris | |
| 5,279,582 A | 1/1994 | Davison et al. | |
| 5,300,041 A | 4/1994 | Haber et al. | |
| 5,318,544 A | 6/1994 | Drypen et al. | |
| 5,328,476 A | 7/1994 | Bidwell | |
| 5,328,486 A | 7/1994 | Woodruff | |
| 5,380,295 A | 1/1995 | Vacca | |
| 5,601,077 A | 2/1997 | Imbert | |
| 5,722,956 A | 3/1998 | Sims et al. | |
| 5,728,075 A | 3/1998 | Levander | |
| 5,743,889 A | 4/1998 | Sams | |
| 5,947,933 A * | 9/1999 | Reichenbach et al. | 604/198 |
| 5,961,495 A | 10/1999 | Walters et al. | |
| 6,096,010 A | 8/2000 | Walters et al. | |
| 6,382,204 B1 | 5/2002 | Jansen et al. | |
| 6,478,779 B1 | 11/2002 | Hu | |
| 6,579,269 B1 | 6/2003 | Kleyman | |
| 6,613,024 B1 | 9/2003 | Gargione | |
| 7,018,365 B2 | 3/2006 | Strauss et al. | |
| 7,901,384 B2 | 3/2011 | Kleyman et al. | |
| 2003/0158525 A1 | 8/2003 | Thorley et al. | |
| 2004/0049161 A1 | 3/2004 | Shearn | |
| 2004/0210200 A1 | 10/2004 | Gerondale et al. | |
| 2006/0247581 A1 | 11/2006 | Pedersen et al. | |

FOREIGN PATENT DOCUMENTS

| | | |
|---|---|---|
| DE | 91 16 022 | 7/1992 |
| EP | 0611 035 A1 | 8/1994 |
| EP | 0 493 639 B1 | 2/1996 |
| EP | 1 459 776 A1 | 9/2004 |
| GB | 2 187 388 | 9/1987 |
| WO | WO 01/19428 A2 | 3/2001 |
| WO | WO 02/22201 | 3/2002 |
| WO | WO 2006/015076 A1 | 2/2006 |

* cited by examiner

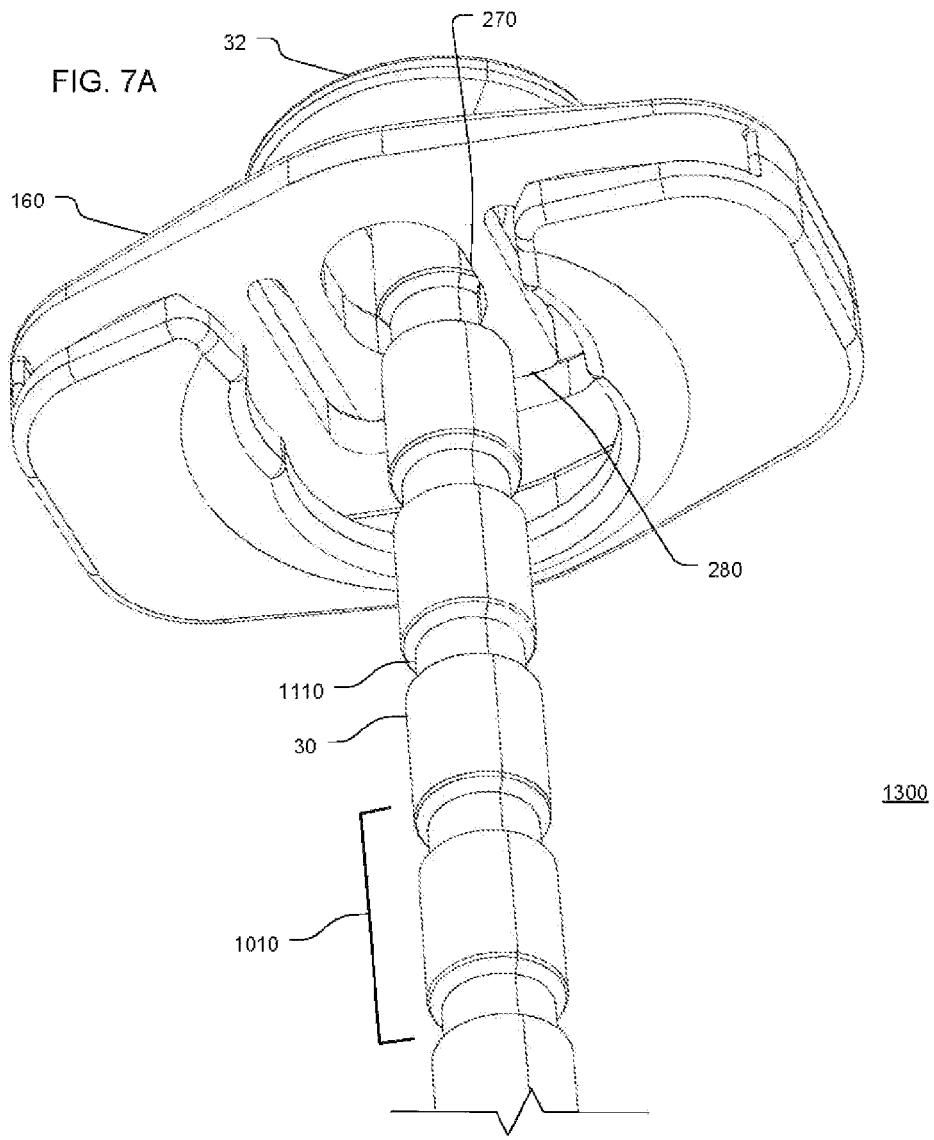

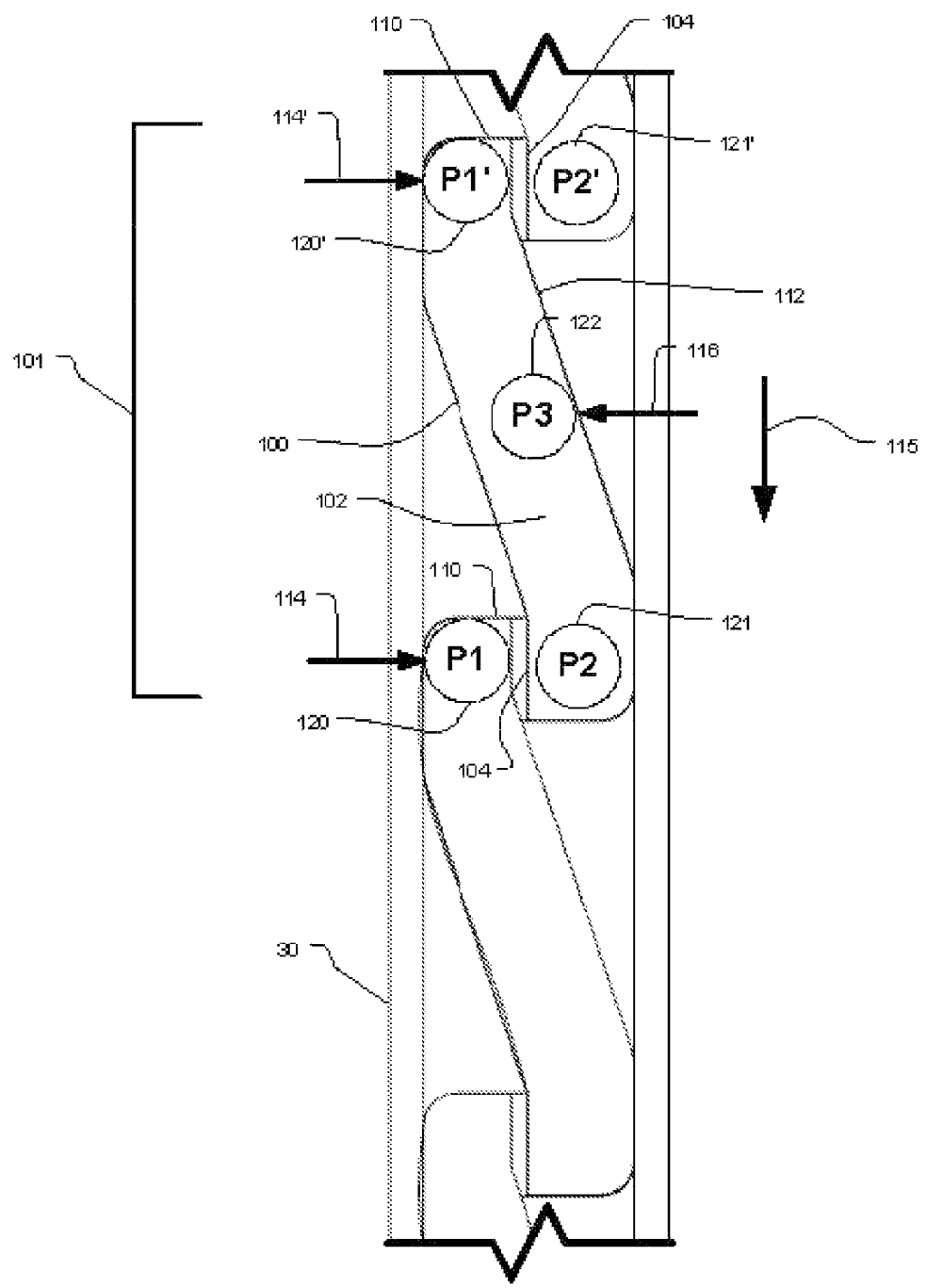

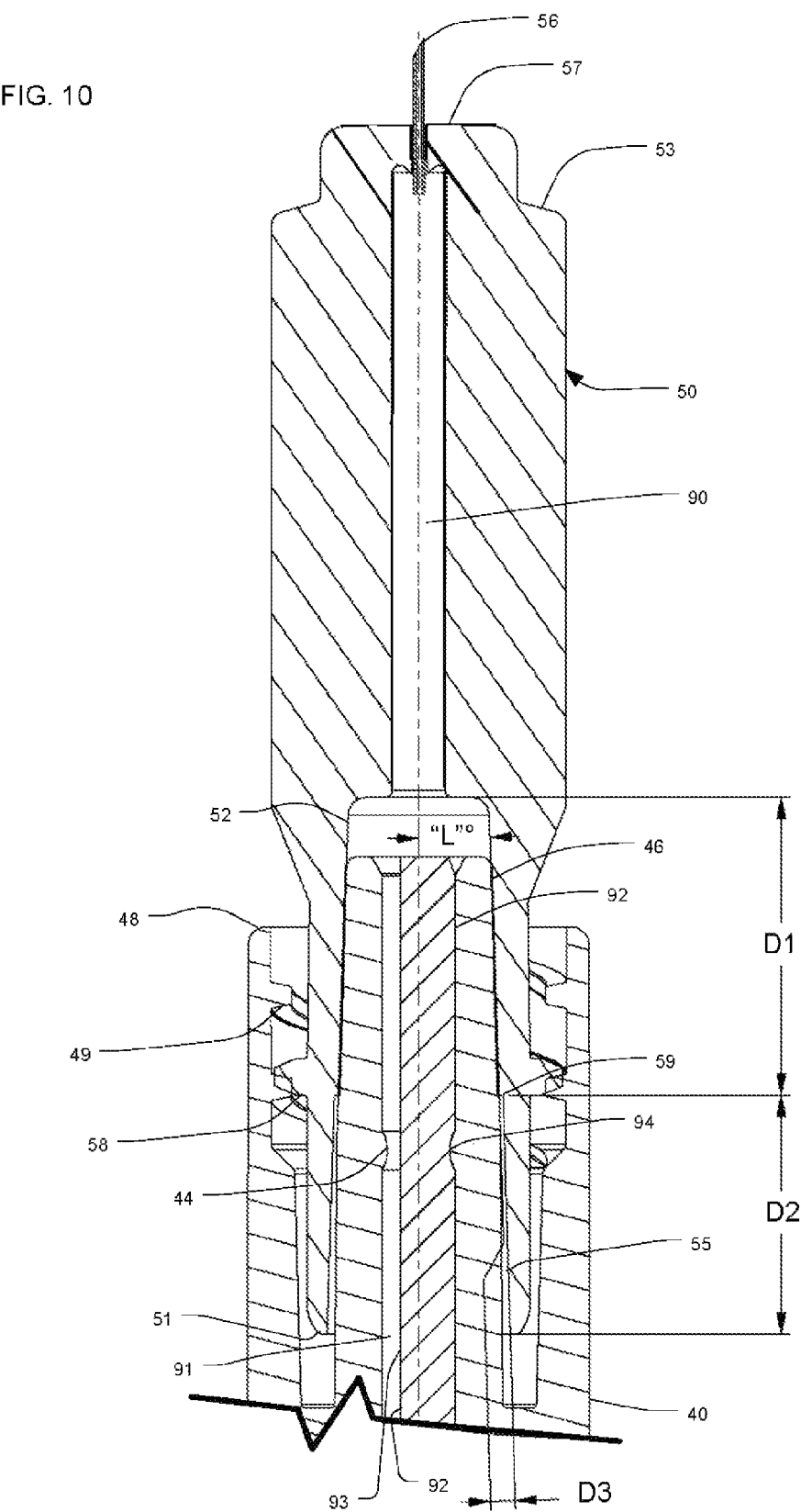

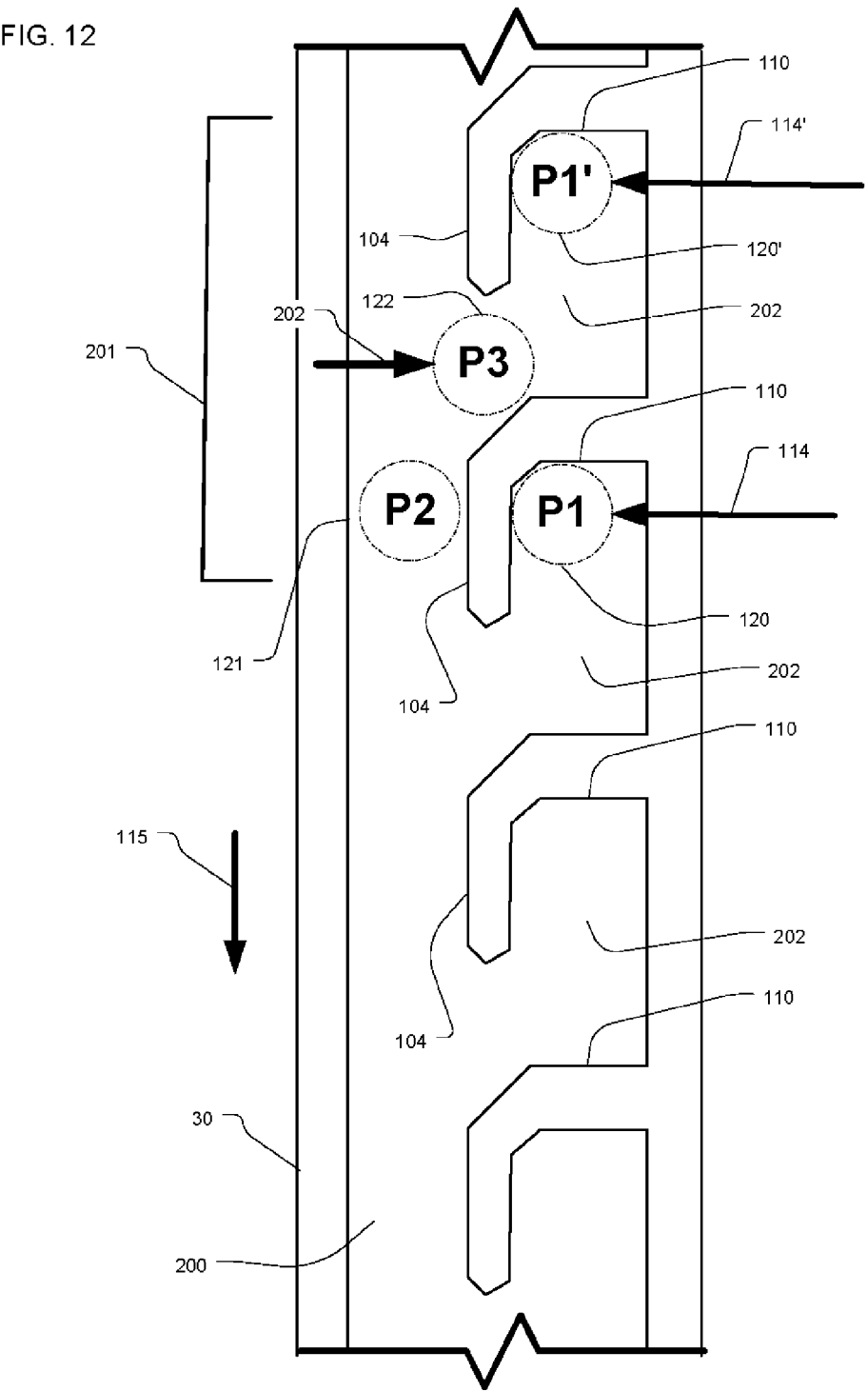

DOSE DIVIDING DELIVERY DEVICE

CROSS REFERENCE TO RELATED APPLICATIONS

This application is a continuation of U.S. patent application Ser. No. 12/864,685 filed Feb. 1, 2011, now abandoned, which is a National Stage Application under 35 U.S.C. §371 of PCT Application No. PCT/IB2008/001028, filed Jan. 30, 2008.

FIELD OF THE INVENTION

The present invention relates generally to delivery devices for delivering substances such as drugs, vaccines and the like, and more specifically relates to a drug delivery system and device having a system for dividing the dose into multiple sub-doses for injection through a needle. More specifically, the present invention relates to a method and apparatus for filling, dosing and disposing an intradermal delivery device using a needle sized for intradermal delivery and a dose divider for dividing the dose for multiple injections using the same needle.

BACKGROUND OF THE INVENTION

Traditionally, syringes are filled by inserting the needle into a vial. The dose is drawn from the vial, pulling the liquid drug dose from the vial into the syringe. The dosage is then expelled from the device by depressing the plunger. If it is desired to divide the total dose into discrete intervals, it must be accomplished manually, or via complicated and costly systems. In the actual usage of devices of this type, multiple doses are given to the same patient at various locations. With a conventional syringe the practitioner must stop depressing the plunger based on visual feedback (from the scale on the syringe). Consequently, it is difficult to perform the repeat dose injections with a high degree of accuracy and/or precision. Furthermore, intradermal injections which can be performed at repeated sites are difficult to perform and adding the difficulty of manually dividing the dose at each site has historically been difficult. Medication pens were developed to produce multiple injections, but are complicated and comprised of many parts. For example, a pen like device is described in U.S. Pat. No. 4,592,745. This pen device is complicated and performs multiple injections but with significant cost. Furthermore, medication pens are not readily adapted for use with fill at time of use systems, especially systems which require reconstitution steps. What is needed is a device and technique for expelling repeated doses from a fill able single syringe to perform multiple injections without having to solely rely on visual feedback from the scale of the syringe, or complicated devices with multiple parts. Furthermore, what is needed is a system that divides the dose that is compatible with conventional reconstitution practices. Attached are the results of a general background search which was conducted for the dose dividers.

SUMMARY OF THE INVENTION

In one embodiment the medication device having aspects of the invention uses a radially moving collar having a cantilevered beam which serves as a pawl. The collar is slidable from a first position to a second position on the flange of the syringe barrel. Furthermore, the plunger of the device is ratcheted with a plurality of spaced detents. In the first position the collar is positioned such that the pawls of the cantilevered beams do not interact with the ratchets of the plunger. A filling needle is attached to the syringe barrel. The first position is the filling position and allows the syringe to be used as a conventional syringe; however, in the usage of this device, the first position primarily serves to fill the syringe using a filling needle without interference by the ratchets. The filling needle is removed from the barrel and an injection needle is attached. The collar is moved to a second position. In the second position the collar is positioned such that the pawls of the cantilevered beams interfere with the detents of the plunger. This position allows the syringe to be used as a multiple repeat dose device. The practitioner inserts the needle into the patient and depresses the plunger. As the plunger is depressed, the pawls interact with the detents which provide for tactile feedback to the practitioner that the discrete intermediate dosage has been delivered. The practitioner then moves the needle to a new injection site and repeats the process. This process continues until the entire dose is delivered.

In another embodiment having aspects of the invention, the device uses a radially slidable component having a follower. The component is slidable from a first position to a second position on the flange of the syringe barrel or on an intermediate part snapped on the syringe flange. Furthermore, the sides of the plunger are grooved with a track having a plurality of spaced units having at least a stop portion. In some embodiments the track has an angled portion, and in others there is a capture portion. In alternate embodiments the track is along the contoured radial surface of the plunger, as the track. In yet another embodiment, the track is configured with units such that the follower is caught in retention areas. In alternate embodiments the plunger contains a plurality of followers and the track is on the slider, thus reversing the location of the features on the parts. In the first position the component is positioned such that the follower of the component does not interact with the tracks of the plunger. Optionally, a filling needle is attached to the syringe barrel. The first position is the filling position and allows the syringe to be used as a conventional syringe; however, in usage of this device the first position primarily serves to fill the syringe using a filling needle (or injection needle) without interference by the follower/tracks. The filling needle is removed from the barrel and an ID injection needle is attached. The component is moved to a second position. In the second position the component is positioned such that the follower of the component is riding in the track of the plunger, and is at the start of an injection cycle. In this case it is at the bottom of a unit. This is the discrete injection position and allows the syringe to be used as a multiple repeat dose device. The practitioner inserts the needle into the patient and depresses the plunger. As the plunger is depressed and begins to move distally, the follower travels along the track. As the follower travels along the angled portion of the track, the component is moved to a third position which is intermediate to the first and second position. At the cusp of the unit, the follower hits a stop point, which is the beginning of the adjacent unit, wherein the plunger is prevented from moving distally. The practitioner then moves the component from the third position to the second position which places the follower at the beginning of angled portion of the adjacent unit. The practitioner then moves the needle to a new injection site and repeats the process. This process continues until the entire dose is delivered.

BRIEF DESCRIPTION OF THE DRAWINGS

Other advantages of the present invention will be readily appreciated as the same becomes better understood by reference to the following detailed description when considered in connection with the accompanying drawings wherein:

FIG. 7A shows a perspective view of a clip and plunger assembly of an alternate embodiment having aspects of the invention.

FIG. 8 shows an enlarged side view of the plunger of FIG. 5.

FIG. 10 shows a cross-sectional view of the hub and barrel assembly of FIG. 3 with the sheath and shield removed for clarity.

FIG. 12 shows an enlarged side view of a plunger used in the embodiment of FIG. 11A-B.

DETAILED DESCRIPTION OF THE PREFERRED EMBODIMENT

Figure 1:
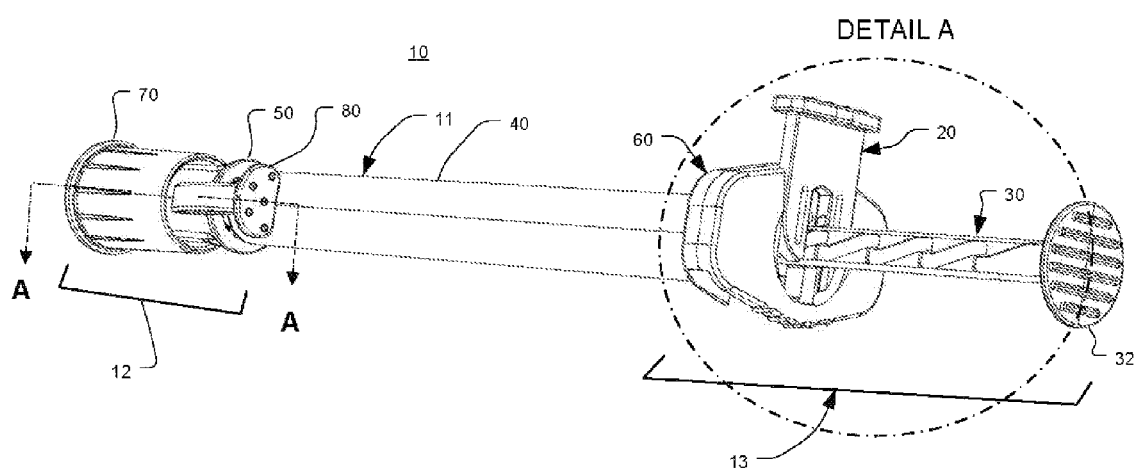
FIG. 1 shows a perspective view of a delivery device having aspects of the invention.

As used herein, the term "proximal" and derivatives thereof, shall mean the end of an item or direction closest to the caregiver during use of the subject invention. The term "distal" and derivatives thereof, shall mean the end of an item or direction towards a patient during use of the subject invention. As used herein, the term "drug substance" and derivatives thereof shall mean any substance that is intended for injection into a patient, including, by way of non-limiting example, drugs, vaccines, therapeutics, and the like. It will be obvious to a person of skill in the art, and from the disclosure provided herein, that the subject invention is not limited or otherwise defined by the type or class of substance administered using the inventive injection device.

For many drug substances, it may be desirable to fill the delivery device at the point of, and immediately prior to use. In this situation, the delivery device is normally filled from a unit dose or multi-dose vial. A multi-dose vial may be more economical and it enables the user to fill the delivery device with the specific dose required. Alternatively, the syringe is pre-filled with a diluent. Alternatively, the syringe is pre-filled with the drug substance, and no filling step is required, and in this case the follower may be pre-set to be within the track. The multi-dose vial may be pre-filled with a liquid substance or with a dry substance. For example, it is now conventional to reduce certain drugs to a dry or powdered form to increase the shelf life of drugs and reduce inventory space. Multi-dose vials are typically sealed with an elastomeric stopper or septum. A needle on the delivery device may be used to pierce the stopper or septum and draw the drug substance from the vial into the delivery device, typically a syringe. The drug substance may then be administered using the delivery device, which is discarded after use, and the unit-dose vial may be stored for further use. Alternatively, the drug substance may be contained in a cryogenic vial. Furthermore, the cryogenic vial may be involved in a complex multi-step reconstitution procedure.

Standard methods for preserving the therapeutic and/or diagnostic substances, such as maintaining them in liquid or powder form in conventional vials for future use, may be used with the intradermal devices of the present invention. The substances for use with the device and method include vaccines and certain medicaments and drugs. Additionally, these substances can be used for diagnostic testing such as, for example, the Mantoux test to determine immunity status against tuberculosis and immediate hypersensivity status of Type I allergic diseases. Also, the substance preferably intradermally delivered in accordance with aspects of the methods and devices of the present invention is selected from the group consisting of drugs, vaccines and the like used in the prevention, diagnosis, alleviation, treatment, or cure of disease, with the drugs including Alpha-1 anti-trypsin, Anti-Angiogenesis agents, Antisense, butorphanol, Calcitonin and analogs, Ceredase, COX-II inhibitors, dermatological agents, dihydroergotamine, Dopamine agonists and antagonists, Enkephalins and other opioid peptides, Epidermal growth factors, Erythropoietin and analogs, Follicle stimulating hormone, G-CSF, Glucagon, GM-CSF, granisetron, Growth hormone and analogs (including growth hormone releasing hormone), Growth hormone antagonists, Hirudin and Hirudin analogs such as hirulog, IgE suppressors, Insulin, insulinotropin and analogs, Insulin-like growth factors, Interferons, Interleukins, Leutenizing hormone, Leutenizing hormone releasing hormone and analogs, Low molecular weight heparin, M-CSF, metoclopramide, Midazolam, Monoclonal antibodies, Narcotic analgesics, nicotine, Non-steroid anti-inflammatory agents, Oligosaccharides, ondansetron, Parathyroid hormone and analogs, Parathyroid hormone antagonists, Prostaglandin antagonists, Prostaglandins, Recombinant soluble receptors, scopolamine, Serotonin agonists and antagonists, Sildenafil, Terbutaline, Thrombolytics, Tissue plasminogen activators, TNF-, and TNF-antagonist, the vaccines, with or without carriers/adjuvants, including prophylactics and therapeutic antigens (including but not limited to subunit protein, peptide and polysaccharide, polysaccharide conjugates, toxoids, genetic based vaccines, live attenuated, reassortant, inactivated, whole cells, viral and bacterial vectors) in connection with, addiction, arthritis, cholera, cocaine addiction, diphtheria, tetanus, HIB, Lyme disease, meningococcus, measles, mumps, rubella, varicella, yellow fever, Respiratory syncytial virus, tick borne japanese encephalitis, pneumococcus, *streptococcus*, typhoid, influenza, hepatitis, including hepatitis A, B, C and E, otitis media, rabies, polio, HIV, parainfluenza, rotavirus, Epstein Barr Virus, CMV, chlamydia, non-typeable haemophilus, moraxella catarrhalis, human papilloma virus, tuberculosis including BCG, gonorrhoea, asthma, atherosclerosis malaria, *E. coli*, Alzheimers, *H. Pylori, salmonella*, diabetes, cancer, herpes simplex, human papilloma and the like other substances including all of the major therapeutics such as agents for the common cold, Anti-addiction, anti-allergy, anti-emetics, anti-obesity, antiosteoporeteic, anti-infectives, analgesics, anesthetics, anorexics, antiarthritics, antiasthmatic agents, anticonvulsants, anti-depressants, antidiabetic agents, antihistamines, anti-inflammatory agents, antimigraine preparations, antimotion sickness preparations, antinauseants, antineoplastics, antiparkinsonism drugs, antipruritics, antipsychotics, antipyretics, anticholinergics, benzodiazepine antagonists, vasodilators, including general, coronary, peripheral and cerebral, bone stimulating agents, central nervous system stimulants, hormones, hypnotics, immunosuppressives, muscle relaxants, parasympatholytics, parasympathomimetrics, prostaglandins, proteins, peptides, polypeptides and other macromolecules, psychostimulants, sedatives, sexual hypofunction and tranquilizers and major diagnostics such as tuberculin and other hypersensitivity agents.

FIG. 1 shows a delivery device having aspects of the invention. Delivery device 10 includes a syringe 11 with a barrel 40 and plunger 30. Plunger 30 is inserted into barrel 40 at the proximal end of device 10. At the distal end of plunger 30 is a stopper which is used to seal barrel 40 to form a reservoir for the drug substance. At the proximal end of plunger 30 is push pad 32. At the distal end of barrel 40 is attached needle assembly 12. Needle assembly 12 is preferably comprised of hub 50 having a needle, sheath 80 and shield 70. Shield 70 is removably attached to the distal end of needle assembly 12. Preferably, needle assembly 12 is attached to barrel 40 via a threaded luer connection, however other connection methods may be used, inter alia luer slip or integral formation. Optional sheath 80 is slidably connected to hub 50 in order to protect the needle after use of the device. Alternatively, a conventional needle assembly may be used such as the type depicted in U.S. Pat. No. 6,494,865 to Alchas, the entire contents of which is incorporated by reference herein, or a standard hypodermic detachable needle. Alternatively, the needle may be integrally assembled onto or into the barrel 40, such that it is a not removable barrel. Typically barrel 40 is plastic but it may be comprised of glass or any other material suitable for drug delivery. At the proximal end of delivery device 10 is dose divider 13. Preferably, dose divider 13 includes a slider 20 and clip 60 which cooperate with plunger 30 to divide the entire dose contained within the syringe 11 into preselected increments. The construction and operation of the dose divider 13 is more readily seen in FIG. 2 and is described below.

Figure 2:
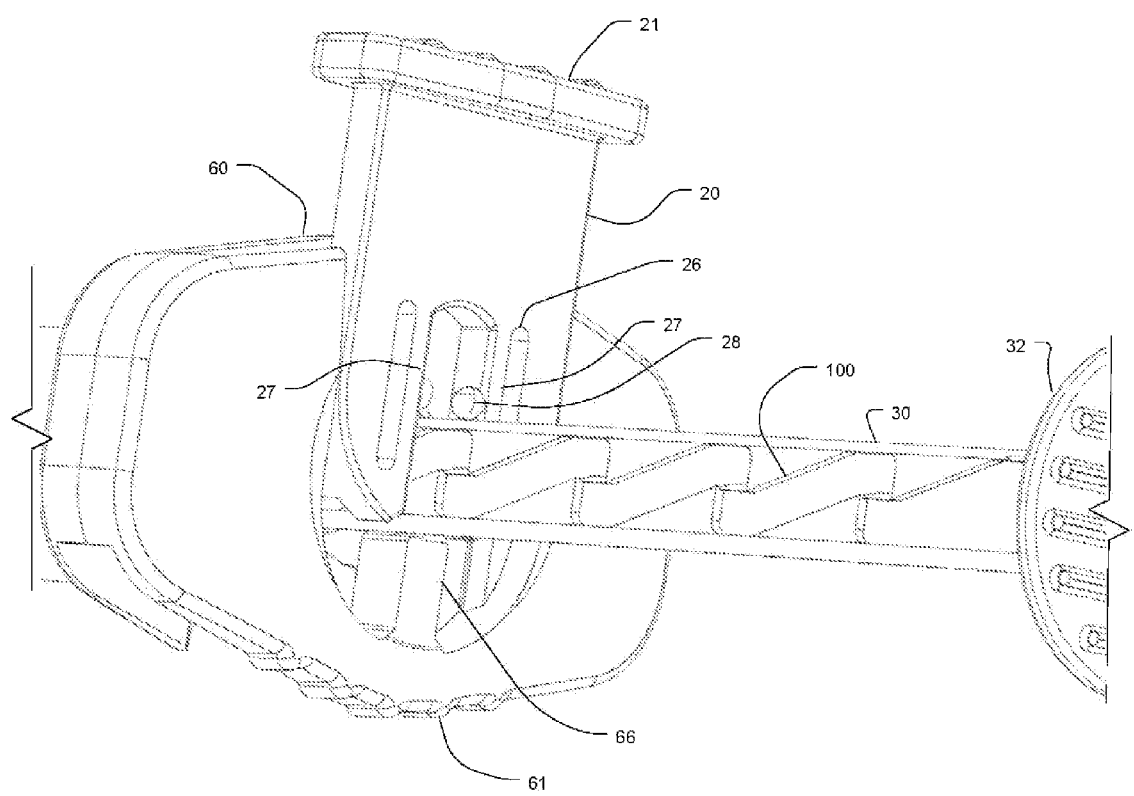
FIG. 2 shows and Enlargement of Detail "A" of the delivery device of FIG. 1.
Figure 4:
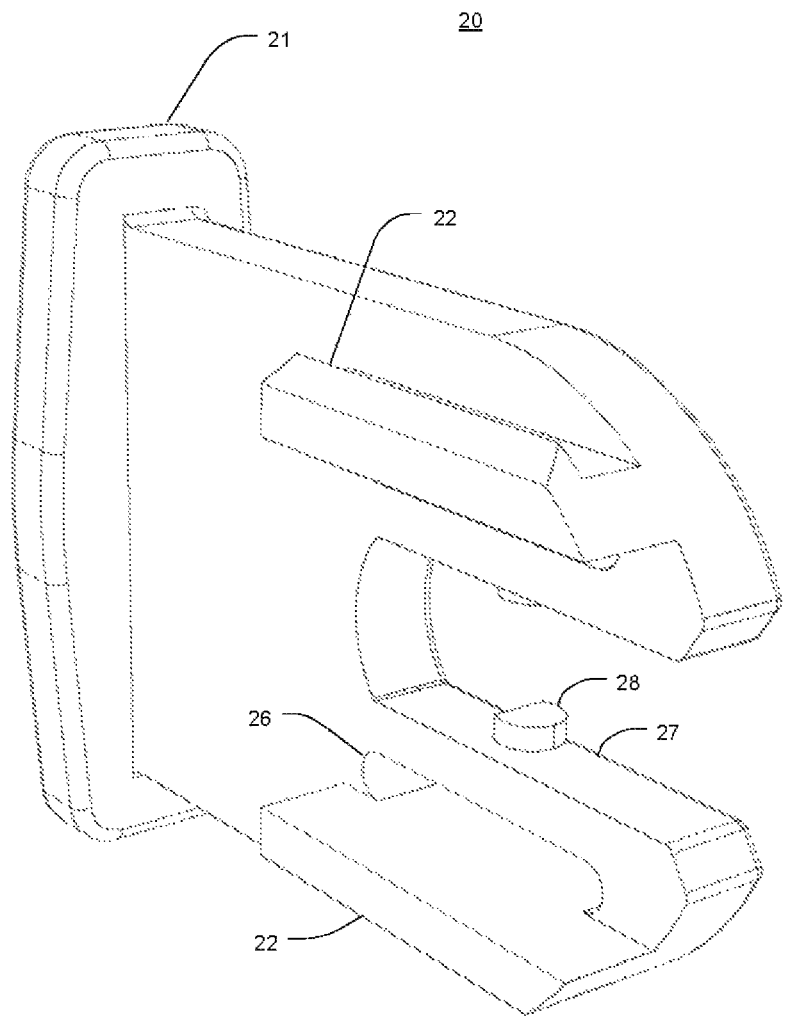
FIG. 4 shows a perspective view of a slider of the embodiment of FIG. 1.

Now turning to FIG. 2, the dose divider 13 includes a slider 20 having a button 21 which is depressible by the health care professional. Slider 20 includes follower 28 which cooperates with track 100 of plunger 30 to divide the entire dose of the drug substance contained in the reservoir of the syringe into discrete unit doses. The unassembled slider is shown in FIG. 4. Slider 20 includes follower 28 which is preferably mounted on deflectable beam 27. In this embodiment opening 26 serves to allow beam 27, and thus follower 28 to deflect in the radial direction. Thus since opening 26 is a closed hole, beam 27 is a double supported beam. Alternatively, opening 26 could be formed such that beam 27 is a cantilevered beam. Alternatively, opening 26 could be omitted such that follower 28 is located on a rigid portion of slider 20, and follower 28 and/or track 100 is elastically deformed and movement on a beam is not required. In this case, the parts would be sized dimensionally such that the interference of the parts was not so great to cause permanent deformation of the parts. Preferably, slider 20 also includes at least one rail 22 which cooperates with features on clip 60 to allow secure slidable engagement between the parts. Follower 28 is a cylindrical protrusion with a portion which is chamfered. Other profiles of protrusions may be used for follower 28. Slider 20 is slidably engaged to clip 60 which is attached to barrel 40. The engagement of slider 20 and clip 60 is shown clearly in FIG. 6. Rails 22 cooperate with opening 62 on the proximal side of clip 60 to provide a secure sliding connection between clip 60 and slider 20. Other slidable connection means may be employed inter alia detents, holes and pins, and slots and followers. Clip 60 optionally includes radial opening 68 which receives a flanged portion of barrel 40. Slider 20 with clip 60 attached to barrel 40 and slider 20 slidably engaged to clip 60, slider 20 is able to be slid in a radial direction with respect to the longitudinal axis of barrel 40, which would extend through barrel opening 69 on distal side of clip 60. Furthermore, substantial proximal and or distal movement of follower 28 with respect to barrel 40 is substantially prevented by the design of slider 20, clip 60 and connection methods employed. Preferably, crush ribs 67 of clip 60 are used to provide a secure connection between flange of barrel 40 and clip 60, which substantially prevents relative movement in the barrel axial direction. Optionally, all of the aspects of Clip 60 described herein would be readily integrally formed into barrel 40, however, for ease of using glass barrels, clip 60 is a separate component, however since the connection of clip 60 to barrel 40 is a connection which prevents any substantial distal or proximal movement of clip 60 to barrel 40, they (clip 60, barrel 40) function as one. Clip 60 optionally includes tactile ribs 61 for gripping by the health care professional. Clip 60 is attached to the distal end of barrel 40, which preferably includes a flange. In this embodiment, Clip 60 is slid radially onto a flange of barrel 40 before insertion of plunger 30 into barrel 40. Clip 60 also preferably includes tang 66 which serves to guide plunger 30 in use of dose divider 30. Now referring back to FIG. 2, for clarity, slider 20 is only shown with follower 28 outside of track 100 of plunger 30. Furthermore, this setting of slider 20 enables use of the syringe 11 as if there were no dose divider 13 attached. In this setting, follower 28 does not interact with track 100 to substantially hinder distal or proximal movement of plunger 30. The dose dividing operation and cooperation of follower 28 and track 100 are further shown in FIGS. 5, 8, and 9A-9B.

Figure 5:
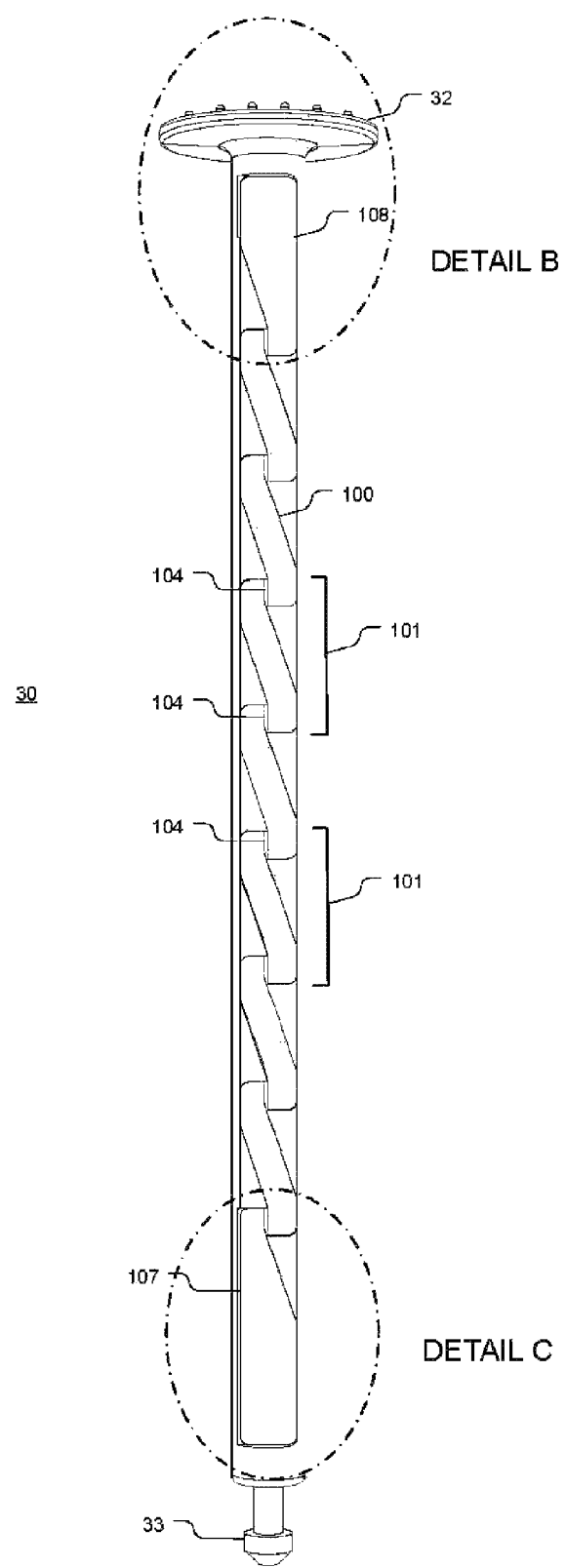
FIG. 5 shows side view of a plunger of the embodiment of FIG. 1.
Figure 6:
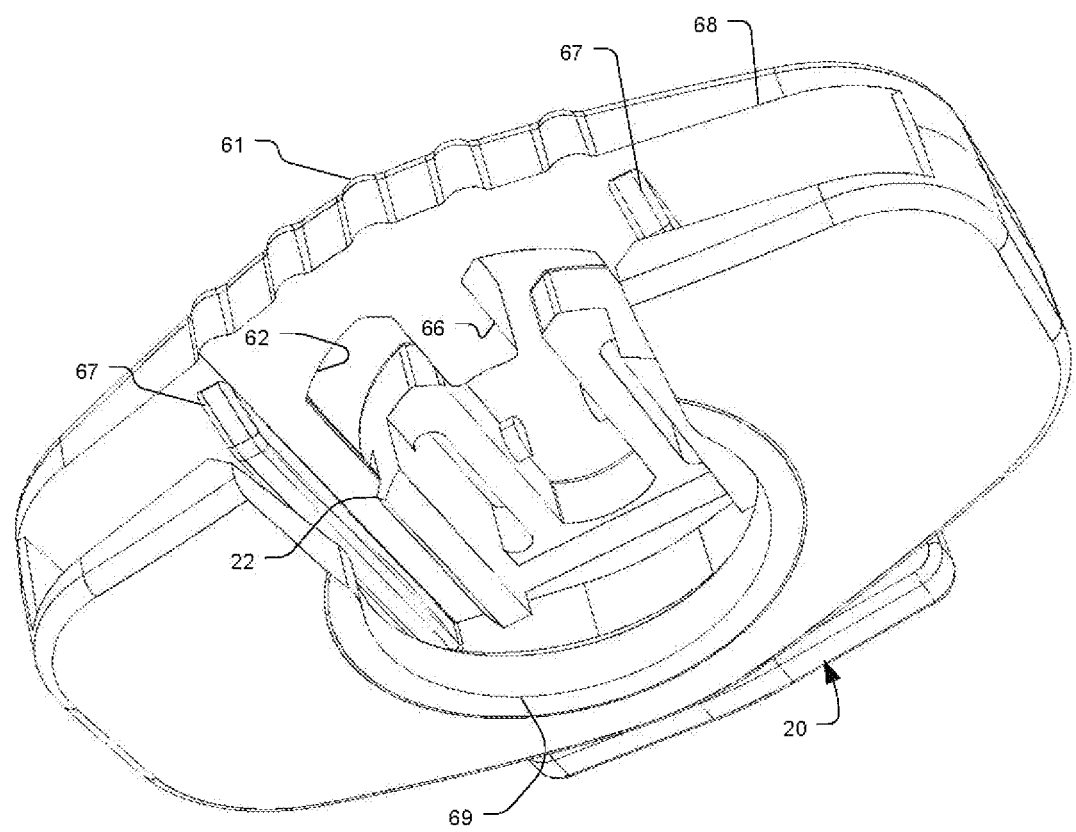
FIG. 6 shows a perspective view of a slider/clip assembly of the device of FIG. 1.
Figure 9A:
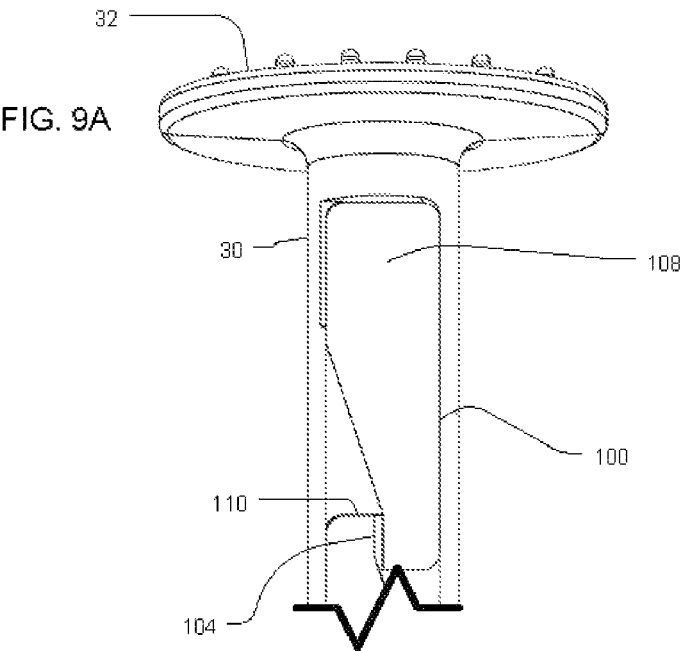
FIGS. 9A and 9B show an enlarged side view of Detail "B" and Detail "C" the plunger of FIG. 5, respectively.
Figure 9B:
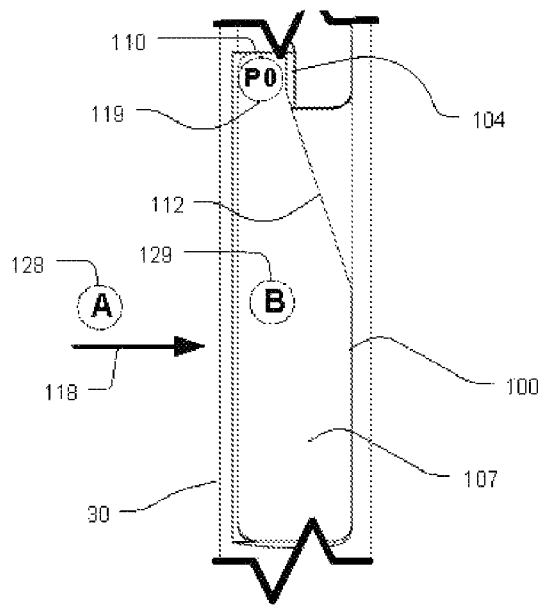

Shown in FIG. 5 is the plunger 30. Plunger 30 comprises distal end with stopper retention means 33, and proximal end with push button 32. Along an exterior surface of plunger 30 is track 100. Track 100 is comprised of one or more discrete units 101 which each of which correspond to a unit dose. The distance between units on Plunger 30 is directly correlated to the amount of substance delivered for each unit. In one embodiment units are of equal size, thus providing equal volumetric unit doses. In an alternate embodiment, the units are differing sizes, thus providing varying volumetric unit doses. Optionally, track 100 includes on distal portion of plunger 30 a starting portion 107. Optionally, track 100 includes on proximal portion of plunger 30 an ending portion 108. These portions are described more fully below and in FIG. 9A-B. In FIG. 9B one can see a detail of starting portion 107 of track 100. The two positions of the follower 28 are represented in FIG. 9B by the position circles labeled A and B, labeled reference numerals 128 and 129, respectively. Position A 128 represents a position of the follower that is outside of track 100. In this position there is no interference of the movement of the plunger 30 by the follower 28. To activate the dose dividing system the follower 28 is biased in the direct of the arrow labeled 118, from position A 128 to position B 129. In position B 129 the follower is within the track, and subject to the guidance of track 100. More specifically the follower 28 is within the starting portion 107 of the track 100; however, it is not mandatory that the follower 28 start in the starting portion 107 of the track 100, only that in order to use the device the follower 28 is within the track 100. In FIG. 9A one can see a detail of finishing portion 108 of track 100 with angled wall 112. Furthermore, the details of the unit 101 are described below and in FIG. 8.

Now turning to FIG. 8, the sides of plunger 30 comprise track 100 with a plurality of spaced units 101. Preferably units 101 are "Z" shaped. Track 100 has angled portions 102 with angled wall portions 112, which are skewed from the longitudinal axis of plunger 30. Track 100 also comprises a plurality of abutting walls 110 which are a portion of track 100 which is substantially perpendicular to the longitudinal axis of plunger 30. Track 100 also preferably comprises a plurality of detent tabs 104 which are aligned substantially parallel to the longitudinal axis of plunger 30. In the first position the slider 20 is positioned such that the follower 28 of the slider 20 does not interact with the track 100 of plunger 30. A filling needle is attached to the syringe barrel. The first position of slider as described above is the filling position and allows syringe 11 to be used as a conventional syringe; however, in usage of delivery device 10 in the first position of slider 20 primarily serves to fill the syringe using either a filling needle or needle assembly 12 without any substantial interference. Thus the plunger 30 may enter the barrel 40 along the length of the plunger 30 with no stoppages. If a filling needle is employed, the filling needle is removed from the barrel and needle assembly 12 is attached in preparation for the unit dosing, after the entire dose is drawn into the barrel 40. In preparation for unit dosing, the slider 20 is moved to a second position in the direction of arrow 114, upon which the follower 28 is now within track 100.

Preferably, the follower 28 is positioned within the track at the starting position 107 (shown in FIG. 9B) which serves as an area to purge the syringe of air and set the plunger to the first unit dose, however, the follower may be placed directly in one of the plurality of units. The health care professional then moves the plunger 30 distally, in the direction of arrow 115. The follower 28 is then directed to position "P0" at the proximal end of starting position 107 via the angled wall 112 of track 100. The dose expelled during this phase is optionally discarded. Alternatively, the dose created during this phase is injected into the patient. When the follower reaches position "P0" labeled as reference numeral 119, the follower 28 abuts abutting wall 110 and distal movement of the plunger is prevented. Position "P0" is the initial position of unit dosing which corresponds to position labeled "P1" identified by reference numeral 120 in FIG. 8. As distal movement of the plunger is prevented by abutting wall 110, the health care professional depresses the slider button 21 to move slider 20 radially in the direction of arrow 114, and reset the dose divider 13. Preferably, follower 28 abuts detent tab 104 which provides resistance to follower 28, thus the slider 20 to move in the radial direction; however, since follower 28 is flexibly mounted on beam 27 of slider 20, movement in the radial direction is possible with deflection of the follower. As discussed previously, a designed deformation of the follower, track or combinations thereof would serve the same purposes. The resistance of the deflection of follower 28 over detent tab 104 is preferably selected so that it gives tactile feedback to the health care professional that the next dose is ready to be delivered. Optionally, the follower 28, beam 27 and detent tab 104 dimensions are selected such that an audible click is heard by the health care professional.

As the follower 28 has now passed detent tab 104, the follower is now at position labeled "P2" identified by reference numeral 121 at the distal end of unit 101. Thus, this is the start of the unit 101 and the start of the delivery of a unit dose. The health care professional inserts the needle 56 into the patient and depresses the plunger 30, preferably by push button 32. As the push button 32 is depressed and the plunger 30 begins to move distally, and since the follower 28 is contained within track 100, the follower 28 travels along the angled portion 102 of track 100. Angled wall 112 biases follower 28 in the direction of arrow 116, and therefore moves slider 120 in the direction of arrow 116. Angled wall 112 serves to cam the follower into another position. At the approximate middle of the unit 101, the follower is now at position labeled "P3" identified by reference numeral 122, in which as the follower 120 travels along the angled portion 102 of track 100, the slider 20 is radially moved proportionally to the distal movement of the plunger 30, dependant on the angle of angled portion 102. As the follower 28 reaches position labeled "P1'" identified by reference numeral 120' at the proximal end of unit 101, the follower 28 reaches a stop point which is the beginning of the adjacent unit 101, wherein the plunger 30 is prevented from moving distally by the interaction of follower 28 and abutting wall 110. Thus, the resetting of the dose divider process is repeated to bring the follower to position labeled "P2'" which is labeled with reference numeral 121'. The practitioner then moves the needle to a new injection site and repeats the process of injection. This process continues until the entire dose is delivered in a series of unit doses. Optionally, the last unit dose has the follower 28 traveling within the ending portion 108 (shown in FIG. 9A) of track 100. In the ending portion 108 there is a large space of track 100 which allows follower 28 of slider 28 to move radially, which indicates to the health care professional that the last dose is delivered. The volumetric unit doses are comprised of the axial distance between positions P2 and P2' multiplied by the area of the cross section of the barrel 40. Preferably, the unit doses are equally spaced, although it would be possible to pre-select unit doses of varying volumes by selecting the spacing of P2 and P2" for each unit 101 of track 100.

Figure 11A:
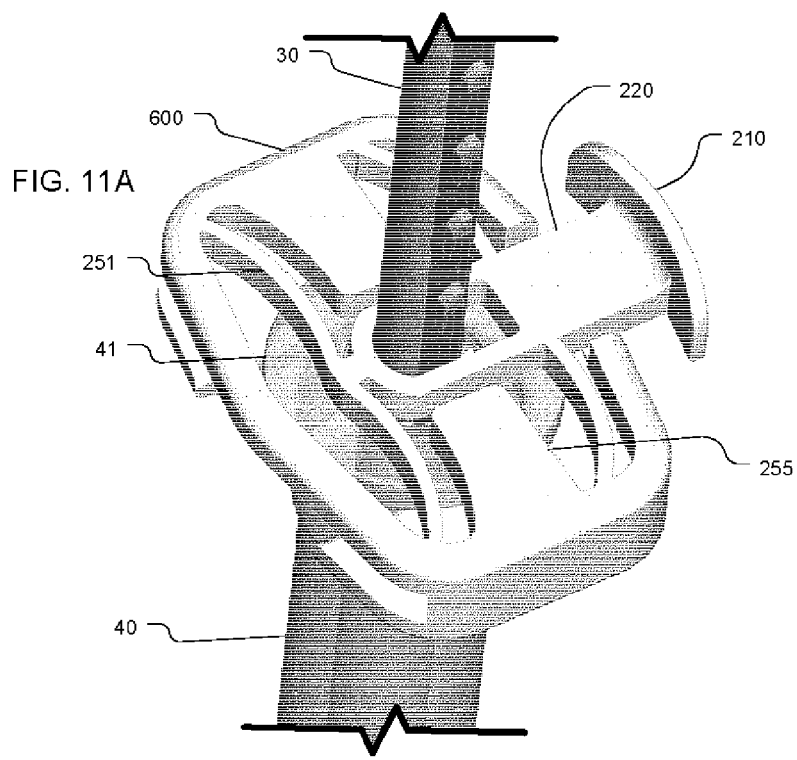
FIG. 11A shows a perspective view of an alternate embodiment of a clip, plunger and barrel having aspects of the invention.
Figure 11B:
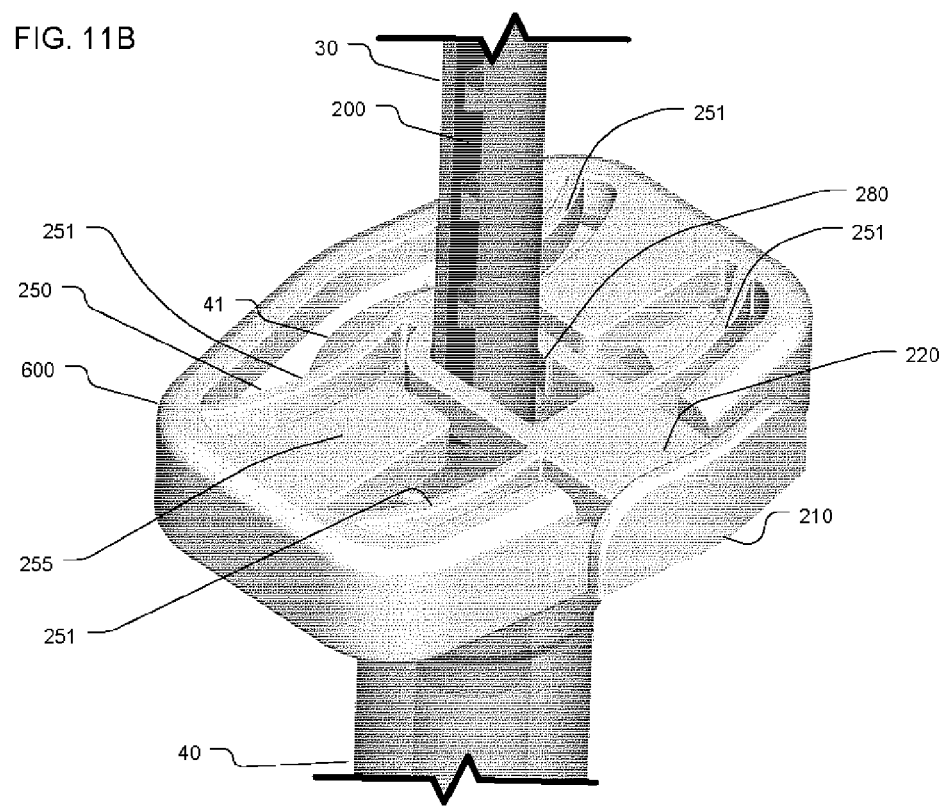
FIG. 11B is a reverse perspective view of the components of FIG. 11A.

Now turning to FIG. 11A-B and FIG. 12 which shows an alternate embodiment of dose divider which is similar to the dose divider as described above. The dose divider of this embodiment contains similar features and operates similarly to the dose divider as described above with a modification in the track and configuration of the unit and the addition of a biasing feature between the slider and the clip. Plunger 30 of this embodiment comprises track 200 having unit 201. Furthermore clip 600 has slider 220 integrally formed therein. Clip 600 is slide onto flange 41 of barrel 40 as described above. Clip 600 also comprises stabilizer 255 which serves to stabilize plunger 30 and slider 220, as well as secure the clip 600 onto the flange 41, or combinations of these purposes. Slider 220 further comprises follower 280. In this embodiment follower 280 is a ratchet-like protrusion on slider 220, although may have other shapes, such as any of the embodiments described herein. Slider 220 is biased radially outward by biasing means 250. In this embodiment biasing means 250 are a series of integrally molded leaf springs 251. Biasing means 250 is designed to place a bias to slider 220 and therefore follower 280 in the operation of the device. Slider 220 also contains optional push button 210. Although Slider 220 is integrally formed with clip 600, slider 220 is able to be slid in a radial direction with respect to the longitudinal axis of barrel 40. Furthermore, substantial proximal and or distal movement of follower 280 with respect to barrel 40 is substantially prevented by the design of slider 220, clip 600 and connection methods employed. Optionally, all of the aspects of Clip 600 described herein would be readily integrally formed into barrel 40, however, for ease of using glass barrels, clip 600 is a separate component, however since the connection of clip 600 to barrel 40 is a connection which prevents any substantial distal or proximal movement of clip 60 to barrel 40, they (clip 60, barrel 40) function as one.

Now turning to FIG. 12, as the follower 280 has three positions (P1, P2, P3) which will be described below. At the beginning of a unit dose, follower is located as position "P1."

In order to begin the dosing sequence, the health care professional depresses button 210 which applies a bias to slider 220 in the direction of arrow 114 and thus forces follower 280 to pass now passed detent tab 104, the follower 280 is now at position labeled "P2" identified by reference numeral 121 at the distal end of unit 201. The health care professional inserts the needle 56 into the patient and depresses the plunger 30, preferably by push button 32. As the push button 32 is depressed and the plunger 30 begins to move distally in the direction of arrow 115, and since the follower 280 is contained within track 200, the follower 28 travels along track 200. However, since there is a bias applied by bias means 250 applied to the slider 220 and follower 280 in the direction in the direction of arrow 202, and therefore moves slider 220 in the direction of arrow 202. At the approximate middle of the unit 201, the follower is now at position labeled "P3" identified by reference numeral 122, in which as the follower 280 travels along track 200, the slider 220 is biased by bias means 250 into the capture portion 202 of track 200. As the follower 280 reaches position labeled "P1'" identified by reference numeral 120' at the proximal end of unit 201, the follower 280 reaches a stop point which is the beginning of the adjacent unit 201, wherein the plunger 30 is prevented from moving distally by the interaction of follower 28 and abutting wall 110. Thus, the resetting of the dose divider process is repeated to bring the follower to position in which the plunger may be moved distally as described above. The practitioner then moves the needle to a new injection site and repeats the process of injection. This process continues until the entire dose is delivered in a series of unit doses. Optionally, the last unit dose has the follower 280 traveling within the ending portion of track 200, similarly as described in the previous embodiment. As in the previous embodiment, the volumetric unit doses are comprised of the axial distance between positions P2 and P2' multiplied by the area of the cross section of the barrel 40. Preferably, the unit doses are equally spaced, although it would be possible to pre-select unit doses of varying volumes by selecting the spacing of P2 and P2" for each unit 201 of track 200.

Figure 7:
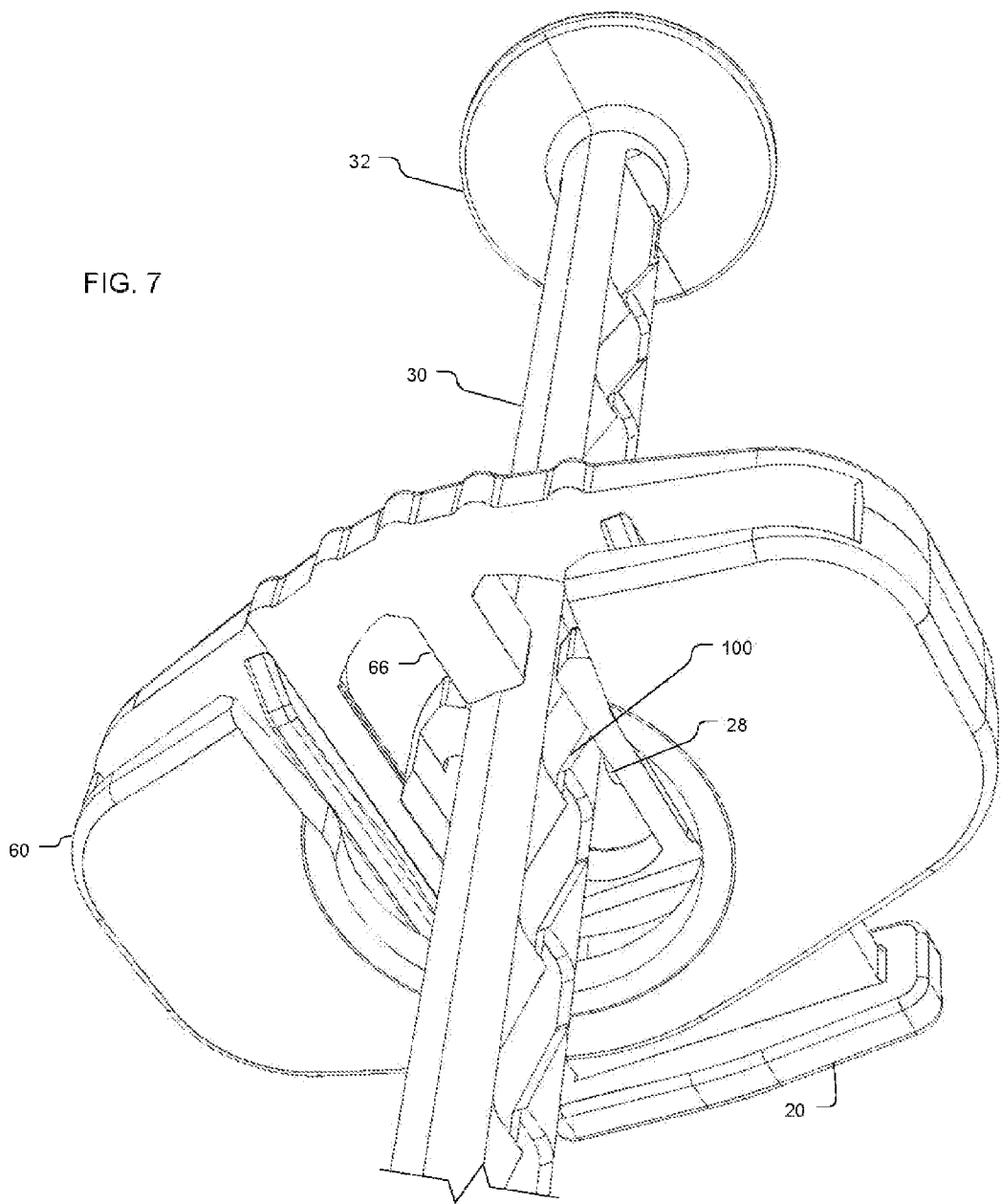
FIG. 7 shows a perspective view of a slider, clip and plunger assembly of the device of FIG. 1.

Now turning to FIG. 7A which shows an alternate embodiment of dose divider 1300 which uses a radially moving collar 160 having a cantilevered beam 270 which serves as a pawl having follower 280. The collar 160 is slidable from a first position to a second position on the flange of the barrel 40. Furthermore, the plunger 30 of the device is ratcheted with a plurality of spaced detents 1110. Detents 1110 are formed into units 1010. In the first position collar 160 is positioned such that the follower 280 of the cantilevered beams 270 do not interact with the detents 1110 of the plunger 30. A filling needle is attached to the syringe barrel. The first position is the filling position and allows the syringe 11 to be used as a conventional syringe; however, in the usage of this device, the first position of collar 160 primarily serves to fill the syringe using a filling needle without interference by the dosing device 1300. The filling needle is removed from the barrel and a needle assembly 12. The collar 160 is moved to a second position on the flange of barrel 40. In the second position the collar 160 is positioned such that the follower 280 of the cantilevered beams 270 interfere with the detents 1110 of the plunger 30. This is the discrete injection position and allows the syringe 11 to be used as a multiple repeat dose device. The practitioner inserts the needle into the patient and depresses the plunger. As the plunger is depressed, the follower 280 interacts with the detents 1110 which provide for tactile feedback to the health care professional that the discrete intermediate dosage has been delivered. The health care professional then moves the needle to a new injection site and repeats the process. This process continues until the entire dose is delivered.

Figure 3:
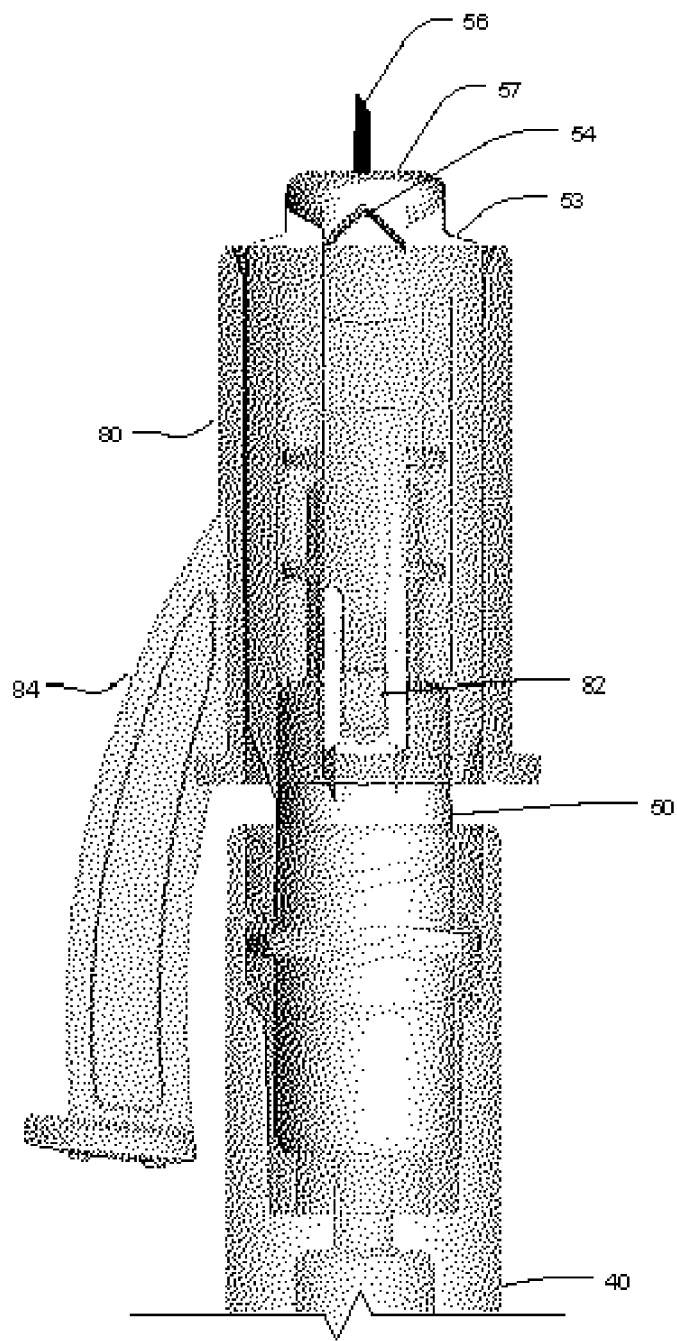
FIG. 3 shows a side view of the distal end of the device of FIG. 1 with the shield of the device removed.

Now turning to FIG. 3 and FIG. 10, the needle assembly 12 includes a needle cannula 56 located at the distal end of the hub 50. In the embodiment depicted in FIGS. 3 and 10, needle 56 is inserted into hub 50 defined at that distal end of needle assembly 12 in a manner known to those skilled in the art. For example, needle 56 may be secured using a friction fit, snap fit, suitable adhesive, solvent weld, or other now known or hereafter developed means of securing a needle to a hub. Sheath 80 is slidably engaged to hub 50 by ribs 53, 54. In one embodiment rib 54 has detents which cooperate with detenting means 82 to lock sheath 80 in at least one of two or more positions. In the intradermal embodiment of needle assembly 12, hub 50 includes a specifically designed skin engaging surface 57, which cooperates with needle 56, extending from the distal end of surface 57 from 0.3 mm to 3 mm, preferably 0.5 mm to 1.5 mm.

FIG. 10 shows a cross section of needle assembly 12 attached to distal end of barrel 40. Barrel 40 comprises collar 48 which contains internal threads 49 which engage with external threads 58 of hub 50. Barrel 40 also comprises luer tip 46 which has a taper of "L" degrees. Typically "L" is approximately between 1.5 and 2.0 degrees. Preferably "L" is approximately 1.75 degrees. Hub 50 also has a corresponding taper within luer opening 51. Preferably, luer opening 51 of hub 50 is adapted to only receive specialized luer tip 46 of barrel 40. Luer opening 51 is designed to have a stepped opening, such that standard luer tips of standard syringes will not fully engage luer opening 51 and thus be un-usable with hub 50 of needle assembly 12. Luer opening 51 is elongated and has a depth dimension of D1+D2. Preferably, dimension D2 is selected such that it is greater than the extension of standard luer tips. More preferably, dimension D2 is selected such that it does not allow engagement of threads 58 into standard luer lock barrels, but the fact that hub proximal end 51 protrudes at distance D2 from threads 58, this does not allow engagement of the components. The interior diameter between D1 and D2 has a discontinuity 59 of dimension D3 such that a step is formed at the interface between D1 and D2. Typically D3 ranges from 0.05 mm to 0.15 mm, preferably approximately 0.1 mm. Typically D1 ranges from 6 mm to 10 mm, preferably approximately 8 mm. Typically D2 ranges from 4.5 mm to 8.5 mm, preferably approximately 6.5 mm. The location of the discontinuity 59 is selected such that effective use of hub 50 on standard luer tips is prevented. Preferably, the location of discontinuity 59 is at the same location as threads 58 along hub 50. However, since the distal end of luer tip 46 is standard in nature, luer tip 46 allows attachment of a standard luer needle with no degradation in performance. As such, luer tip 46 allows both use of a standard luer needle for filling and hub 50 of specialized needle assembly 12 for injection.

Preferably inserted in the internal diameter of luer tip 46 is restrictor pin 92. Restrictor pin 92 is substantially cylindrical and comprises a flattened portion 93 such that when restrictor pin 92 is inserted into internal diameter of luer tip 46, the internal diameter is substantially but not completely obstructed to form flow path 91. Preferably flow path 91 is sized to enable effective filling of delivery device 10 and prevent excessive shear forces on any substances delivered. Restrictor pin 92 also optionally comprises detent 94 which cooperates with optional detent rib 44 within luer tip 46 which serves to retain restrictor pin 92 in luer tip 46. Other methods may be used to retain restrictor pin 92 in luer tip 46. Hub 50 has dead space 90 which is included of the overall dead space of the system. It may be desirable to add a second restrictor pin within hub dead space 90, as well. Alternatively, an elongated restrictor pin of similar design may be used in both spaces. Thus, restrictor pin 46 serves to reduce the overall "dead space" of delivery device 10.

In use, a health care professional administering the injection will unwrap the protective packaging from the vial. The health care professional will then manually insert the medication device into the vial in preparation for aspiration of medication into barrel 40. If supplied as separate components, the health care professional will then manually insert the syringe 11 into the filling needle in preparation for aspiration of medication. Alternatively, the filling needle and delivery device 10 are pre-assembled in a kit supplied with needle assembly 12. In another embodiment, all three components (needle assembly 12, syringe 40 and the filling needle are supplied in a kit. In another embodiment, syringe 40 is pre-filled with the drug substance and no filling is required. In another embodiment, syringe 40 is pre-filled with a diluent. Optionally, at this point, a diluent is injected in the medication vial. The healthcare professional then aspirates the syringe with the medication from the medication vial from syringe 11. The health care professional will then manually remove the syringe 11 from the filling needle in preparation for administration of the injection. The needle assembly 12 is then attached to the device. In another embodiment, the filling needle is the same needle as the needle assembly 12. Administration will, in one embodiment, involve pressing the skin engaging surface 57 of the hub 50 substantially perpendicular to a surface of the patient's skin. The first unit dose of the drug substance will then be injected using the plunger 30. As the plunger is depressed the follower of the dose divider 13 follows the path of the track 100,200. The follower then reaches stop point 122. Upon completion of the unit dose, the health care professional withdraws the needle cannula from the patient's skin and prepares to reset the dose divider. Optionally the health care professional prepares the next injection site. The dose divider 13 is then reset in order to deliver the next unit dose, which entails moving the follower to start point 120. Preferably, the reset involves pushing a button on the slider such that the follower is moved into the start point 120. This cycle is then repeated for the number of units along the length of the plunger. Upon completion of the entire dose, the health care professional withdraws the needle cannula from the patient's skin and disposes the used injection device 10 in a suitable container. Prior to disposal, the health care professional optionally activates the shielding portion of delivery device by sliding sheath 80 distally.

As will now be understood, the delivery device having aspects of the invention may include a needle enclosure means which encloses or conceals the needle cannula tip following injection and which preferably cannot be retracted to prevent accidental needle contact or reuse. In the embodiment shown in FIGS. 1 and 3, a sheath 80 may be extended following injection and locked in place. The assembly includes sheath 80 which locks in the extended position, preventing contact with the needle by use of locking means 82. Optionally arm 84 extends for the main potion of sheath 80 to aid in activation.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, wherein reference numerals are merely for convenience and are not to be in any way limiting, the invention may be practiced otherwise than as specifically described.

What is claimed is:

1. A multiple dose injection device comprising:
   a fluid conduit;
   a barrel having a bore, a distal end, and a proximal end wherein the fluid conduit is located at the distal end of the barrel, in fluid communication with the bore and the proximal end of the barrel is adapted to receive a stopper;
   a plunger having a distal end and a proximal end and a longitudinal axis wherein the stopper is connected to the distal end of the plunger and movable within the barrel, and the plunger has at least one continuous track formed between the distal and proximal ends of the plunger wherein the at least one continuous track further comprises at least one of each of the following:
      a first rest position,
      a stop position, having a proximal abutment,
      a second rest position,
      a camming portion which is skewed to the longitudinal axis of the plunger and formed between the first rest position and the stop position;
      a reset portion substantially perpendicular to the axis of the plunger and formed between the stop position and the second rest position; and,
   a slider having a follower movable substantially perpendicular to the axis of the plunger, the slider having a user-pressable portion;
      wherein when a portion of the plunger is depressed by a user, the follower moves with respect to the plunger along the camming portion of the at least one continuous track, thereby causing radial motion of the follower and movement of the follower to the stop position at which position a plunger distal movement is prevented by contact of the follower to the proximal abutment, wherein the user may apply a biasing force to the user-pressable portion of the slider, thereby moving the follower along the reset portion to the second rest position.

2. The device as set forth in claim 1 wherein the follower is movable from an initial position wherein the follower is located outside of the at least one continuous track and does not interfere with the plunger movement, to a first position wherein the follower is located within the at least one continuous track.

3. The device as set forth in claim 1 wherein a pattern of the first rest position, stop position, and second rest position are repeated along the plunger at an axial distance between corresponding positions, wherein said axial distance multiplied by a cross sectional area of the bore is a unit volume which comprises a unit dose.

4. The device as set forth in claim 3 wherein the unit dose is a plurality of unit doses and all unit doses are substantially equal.

5. The device as set forth in claim 3 wherein the unit dose is a plurality of unit doses and all unit doses are of varying dosages.

6. The device as set forth in claim 1 further comprising a clip which engages a flange on the barrel and the slider is slidably engaged to the clip.

7. The device as set forth in claim 6 the clip further comprising a plunger guiding portion.

8. The device as set forth in claim 6 wherein the clip and slider are integrally formed with a slidable relationship.

9. The device as set forth in claim 1 wherein the at least one continuous track further comprises two tracks, located on opposing sides of the plunger.

10. The device as set forth in claim 1 wherein the at least one continuous track is a helical track around a circumference of the plunger.

11. The device as set forth in claim 1 wherein the follower is mounted on a deflectable beam.

12. The device as set forth in claim 11 wherein the reset portion further comprises a detent tab located in the at least one continuous track which deflects the follower.

13. The device as set forth in claim 12 wherein the deflection creates an audible sound, thereby providing feedback to the user.

14. The device as set forth in claim 11 wherein the reset portion further comprises a deflectable detent tab located in the at least one continuous track.

15. The device as set forth in claim 1 wherein the follower is elastically deformed in use.

16. The device as set forth in claim 1 wherein the fluid conduit further comprises a detachable needle assembly having a hub, attachable to the distal end of the barrel and a needle inserted into the hub.

17. The device as set forth in claim 16 wherein the hub further comprises a proximal opening adapted to receive an elongated luer tip located at the distal end of the barrel and is adapted to prevent effective use of a standard luer tipped barrel.

18. The device as set forth in claim 1 further comprising a restrictor pin within the fluid conduit thereby reducing dead space.

19. The device as set forth in claim 1 further comprising a hub engaged to the barrel having a needle cover removably attached to said hub.

20. The device as set forth in claim 19 further comprising a shield which is slidably engaged to the hub.

21. A multiple dose injection device comprising:
a fluid conduit;
a barrel having a bore, a distal end, and a proximal end wherein the fluid conduit is located at the distal end of the barrel, in fluid communication with the bore and the proximal end of the barrel is adapted to receive a stopper;
a plunger having a distal end and a proximal end and a longitudinal axis wherein the stopper is connected to the distal end of the plunger and movable within the barrel, and the plunger has at least one continuous track formed between the distal and proximal ends of the plunger wherein the at least one continuous track further comprises at least one of each of the following:
a first rest position,
a stop position, having a proximal abutment,
a second rest position,
a capturing portion formed between the first rest position and the stop position;
a reset portion substantially perpendicular to the axis of the plunger and formed between the stop position and the second rest position; and,
a slider having a follower movable substantially perpendicular to the axis of the plunger, the slider having a user-pressable portion;
wherein the follower is biased toward the stop position, thereby radially biasing the follower in the capturing portion to the stop position at which position a plunger distal movement is prevented by contact of the follower to the proximal abutment, wherein a user may apply a reverse biasing force to the user-pressable portion of the slider, thereby moving the follower along the reset portion to the second rest position.

22. The device as set forth in claim 21 wherein the follower is movable from an initial position wherein the follower is located outside of the at least one continuous track and does not interfere with the plunger movement, to a first position wherein the follower is located within the at least one continuous track.

23. The device as set forth in claim 21 wherein a pattern of the first rest position, stop position, and second rest position are repeated along the plunger at an axial distance between corresponding positions, wherein said axial distance multiplied by a cross sectional area of the bore is a unit volume which comprises a unit dose.

24. The device as set forth in claim 23 wherein the unit dose is a plurality of unit doses and all unit doses are substantially equal.

25. The device as set forth in claim 23 wherein the unit dose is a plurality of unit doses and all unit doses are of varying dosages.

26. The device as set forth in claim 21 further comprising a clip which engages a flange on the barrel and wherein the clip and the slider are integrally formed with a slidable relationship therebetween.

27. The device as set forth in claim 26 further comprising integrated leaf springs which are integrally molded.

28. The device as set forth in claim 21 wherein the at least one continuous track further comprises two tracks, located on opposing sides of the plunger.

29. The device as set forth in claim 21 wherein the follower is mounted on a deflectable beam.

30. The device as set forth in claim 29 wherein a deflection of said deflectable beam creates an audible sound, thereby providing feedback to the user.

31. The device as set forth in claim 21 wherein the fluid conduit further comprises a detachable needle assembly having a hub, attachable to the distal end of the barrel and a needle inserted into the hub.

32. A method of performing a multiple dose delivery comprising:
providing a device comprising a fluid conduit; a barrel having a bore, a distal end, and a proximal end wherein the fluid conduit is located at the distal end of the barrel, in fluid communication with the bore and the proximal end of the barrel is adapted to receive a stopper; a plunger connected to the stopper and movable within the barrel, thereby forming a reservoir, the plunger having a longitudinal axis and at least one continuous track formed between a distal end of the plunger and a proximal end of the plunger wherein the at least one continuous track further comprises at least one of each of the following:
a first rest position,
a stop position, having a proximal abutment,
a second rest position,
a camming portion not parallel to the longitudinal axis of the plunger and formed between the first rest position and the stop position;
a reset portion substantially perpendicular to the axis of the plunger and formed between the stop position and the second rest position; and,
a slider having a follower and a user depressable portion;
filling the reservoir of the device with a fluid;
moving the slider from an initial position wherein the follower is located outside of the at least one continuous track and does not interfere with plunger movement, to a first position wherein the follower is located within the at least one continuous track;

depressing a portion of the plunger to dispense a portion of the fluid through the fluid conduit and thereby moving the follower with respect to the plunger along the camming portion of the at least one continuous track, thereby causing radial motion of the follower and movement of the follower to the stop position wherein a plunger distal movement is prevented by contact of the follower to the proximal abutment;

applying a biasing force to the user-pressable portion of the slider, thereby moving the follower along the reset portion to the second rest position which coincides with the first rest position; and, repeating the depressing and applying steps until all the fluid is dispensed from the reservoir.

\* \* \* \* \*